US011049252B2

(12) United States Patent
Miyazaki et al.

(10) Patent No.: US 11,049,252 B2
(45) Date of Patent: Jun. 29, 2021

(54) MOVING OBJECT TRACKING APPARATUS, RADIOTHERAPY SYSTEM AND MOVING OBJECT TRACKING METHOD (71) Applicant: Hitachi, Ltd., Tokyo (JP)

(72) Inventors: Koichi Miyazaki, Tokyo (JP); Toru Umekawa, Tokyo (JP); Yusuke Fujii, Tokyo (JP)

(73) Assignee: HITACHI, LTD., Tokyo (JP)

( * ) Notice: Subject to any disclaimer, the term of this patent is extended or adjusted under 35 U.S.C. 154(b) by 24 days.

(21) Appl. No.: 16/703,987

(22) Filed: Dec. 5, 2019

(65) Prior Publication Data

US 2021/0012500 A1 Jan. 14, 2021

(30) Foreign Application Priority Data

Jul. 8, 2019 (JP) .............................. JP2019-126894

(51) Int. Cl.
*G06T 7/00* (2017.01)
*G06T 7/70* (2017.01)
(Continued)

(52) U.S. Cl.
CPC ......... *G06T 7/0016* (2013.01); *G01N 23/043* (2013.01); *G06T 5/10* (2013.01);
(Continued)

(58) Field of Classification Search
USPC .............................................. 382/103, 1, 28
See application file for complete search history.

(56) References Cited

U.S. PATENT DOCUMENTS 6,307,914 B1 * 10/2001 Kunieda .................. A61B 6/12
378/65
8,682,414 B2 * 3/2014 Nishimoto ............. A61N 5/103
600/425
(Continued)

FOREIGN PATENT DOCUMENTS

JP 2017-124300 A 7/2017
JP 2017-196036 A 11/2017
(Continued)

OTHER PUBLICATIONS

Extended European Search Report received in corresponding European Application No. 19215173.6 dated Jun. 9, 2020.

*Primary Examiner* — Ishrat I Sherali
(74) *Attorney, Agent, or Firm* — Mattingly & Malur, PC (57) ABSTRACT The moving object tracking apparatus emphasizes an image with specific size in each of fluoroscopic images derived from two or more paired fluoroscopic radiographic devices, obtains a value indicating certainty degree of detecting a candidate position of the object to be tracked on the image subjected to the emphasizing process, extracts the candidate position based on the value indicating the certainty degree of detection, calculates a value indicating a correlation between the candidate position extracted from images picked up from two or more directions, and a position of the fluoroscopic radiation generator, detects the position of the object to be tracked based on the value indicating the certainty degree of detection, and the value indicating the correlation, and controls irradiation of radiation to an irradiation target based on the detected position of the object to be tracked.

13 Claims, 8 Drawing Sheets (51) Int. Cl.
  *G01N 23/04* (2018.01)
  *G06T 5/10* (2006.01)
  *G06T 7/20* (2017.01)
(52) U.S. Cl.
  CPC .............. *G06T 7/20* (2013.01); *G06T 7/70* (2017.01); *G06T 2207/10121* (2013.01); *G06T 2207/30004* (2013.01)

(56) References Cited

U.S. PATENT DOCUMENTS

| | | | | |
|---|---|---|---|---|
| 9,724,049 B2* | 8/2017 | Umekawa | ............ | A61B 6/5294 |
| 10,737,117 B2* | 8/2020 | Mori | ............ | A61N 5/1037 |
| 2007/0211857 A1* | 9/2007 | Urano | ............ | A61N 5/1049 378/65 |
| 2007/0297566 A1* | 12/2007 | Urano | ............ | A61N 5/1049 378/65 |
| 2010/0316259 A1* | 12/2010 | Liu | ............ | G06T 7/246 382/107 |
| 2011/0196230 A1* | 8/2011 | Nishimoto | ............ | A61N 5/103 600/427 |
| 2012/0041250 A1* | 2/2012 | Ishikawa | ............ | A61B 6/12 600/1 |
| 2014/0018604 A1* | 1/2014 | Ishikawa | ............ | A61N 5/1049 600/1 |
| 2015/0036793 A1* | 2/2015 | Umekawa | ............ | A61N 5/1049 378/8 |
| 2017/0304649 A1* | 10/2017 | Sumita | ............ | A61N 5/10 |
| 2017/0348061 A1* | 12/2017 | Joshi | ............ | A61M 5/172 |
| 2019/0060672 A1* | 2/2019 | Takahashi | ............ | A61B 6/548 |
| 2019/0111282 A1* | 4/2019 | Yamada | ............ | A61B 6/12 |
| 2019/0143146 A1* | 5/2019 | Fujii | ............ | A61B 6/022 600/1 |
| 2019/0175941 A1* | 6/2019 | Miyazaki | ............ | A61B 6/5217 |
| 2020/0005472 A1* | 1/2020 | Terunuma | ............ | A61N 5/1049 |
| 2020/0155870 A1* | 5/2020 | Takahashi | ............ | A61N 5/1067 |
| 2021/0035293 A1* | 2/2021 | Hirai | ............ | A61N 5/1049 |

FOREIGN PATENT DOCUMENTS

JP 2017-209243 A 11/2017
WO 2014/041909 A1 3/2014

* cited by examiner

| CANDIDATE NO.61A | CANDIDATE NO.62A | LENGTH OF COMMON PERPENDICULAR LINE | EVALUATION FUNCTION |
|---|---|---|---|
| 71A | 73A | 2.1 | 120 |
| 72A | 73A | 5.8 | 100 |

FIG. 7B

| CANDIDATE NO.61B | CANDIDATE NO.62B | LENGTH OF COMMON PERPENDICULAR LINE | EVALUATION FUNCTION |
|---|---|---|---|
| 71B | 73B | 3.4 | 130 |
| 72B | 73B | 4.0 | 150 |
| 75B | 73B | 2.1 | 120 |
| 71B | 74B | 0.1 | 180 |
| 72B | 74B | 5.8 | 100 |
| 75B | 74B | 1.2 | 140 |

MOVING OBJECT TRACKING APPARATUS, RADIOTHERAPY SYSTEM AND MOVING OBJECT TRACKING METHOD

The present application claims priority from Japanese application JP 2019-126894, filed on Jul. 8, 2019, the contents of which is hereby incorporated by reference into this application.

BACKGROUND

The present invention relates to a moving object tracking apparatus configured to recognize a target position in a subject in real time, a radiotherapy system for irradiating therapeutic radiation using the moving object tracking apparatus, and a moving object tracking method.

In the disclosure of Japanese Unexamined Patent Application Publication No.2017-209243, the template image with markers is prepared for template matching on two fluoroscopic images. The positions with high matching scores are listed as candidate positions of the marker. Each length of common perpendicular lines is calculated with respect to all combinations of two candidate positions of the marker in the list. Based on the matching scores and the common perpendicular lines, the marker position is detected. Based on the detected marker position, extraction of proton beam to be irradiated to the target is controlled.

Japanese Unexamined Patent Application Publication No. 2017-124300 discloses the medical image processor that includes a calculation unit and a detection unit. The calculation unit sets a first region that includes two or more first pixels around each interest pixel of the fluoroscopic image in the subject, and a second region that includes one or more second pixels different from the two or more first pixels so that the likelihood is calculated. The likelihood is the value that becomes large as pixel values of those two or more first pixels approximate to one another, and the pixel values of two or more first pixels and the pixel values of one or more second pixels are separated further. Based on each likelihood value of the interest pixel, the object position in the subject is detected.

Japanese Unexamined Patent Application Publication No. 2017-196036 discloses the moving object tracking control apparatus is configured to execute the gradation process to pickup images A and B. Using the gradation processed pickup images A and B, the marker position is calculated. The signal for controlling radiation irradiation is generated based on the marker position.

SUMMARY

High accuracy radiotherapy has been required to control the therapeutic radiation irradiation apparatus in accordance with fluctuation in the position and the shape of the affected part owing to motions in the subject body such as respiration and heartbeat. The real-time tumor tracking radiotherapy has been known as the method of irradiating the therapeutic radiation with high accuracy.

The real-time tumor tracking radiotherapy is conducted to locate the target such as the marker detained in the affected part and the patient body in reference to the fluoroscopic image of the inside of the patient body picked up using X-ray and the like. In the following description, the radiation for treatment will be referred to as "therapeutic radiation", and the radiation for measurement of the target position will be referred to as "fluoroscopic radiation" for distinction therebetween.

In the case of low intensity of the fluoroscopic radiation, noise contained in the fluoroscopic image is increased, leading to misrecognition as a result of detecting the object other than the target. The intensity of the fluoroscopic radiation has to be high to some extent to prevent the misrecognition. This may cause increase in the operation load to the fluoroscopic radiation irradiation apparatus.

The misrecognition owing to noise may be prevented by the known process disclosed in the documents as described above.

In the disclosure of Japanese Unexamined Patent Application Publication No. 2017-209243, the misrecognition owing to noise may be prevented. It is expected to decrease the operation load to the fluoroscopic radiation detector is expected.

In the disclosure of Japanese Unexamined Patent Application Publication No. 2017-124300, as the target may be detected even if the intensity of the fluoroscopic radiation is lowered, it is expected to decrease the operation load of the fluoroscopic radiation detector.

In the disclosure of Japanese Unexamined Patent Application Publication No. 2017-196036, as the marker may be continuously tracked without being missed even in the presence of the marker-like structure near the marker. Upon missing of the marker, the operator does not have to operate the moving object tracking apparatus to redetect the marker.

It has been found, however, that the technique as disclosed in those documents has to be further improved from the viewpoint to be described below.

In the disclosure of Japanese Unexamined Patent Application Publication No. 2017-209243, it has been discovered that the template matching fails to list the candidate positions of the target because of excessive noise. Therefore, the intensity of the fluoroscopic radiation has to be kept high to the degree sufficient to allow listing of the candidate positions of the target derived from the template matching.

In the disclosure of Japanese Unexamined Patent Application Publication No. 2017-124300, it has been discovered that the excessive noise largely distorts the projected image of the target from its original shape, thus lowering the likelihood at the marker position. As a result, the image with similar shape to that of the target, which has been incidentally generated by the noise may be misrecognized. In order to prevent such misrecognition, the intensity of the fluoroscopic radiation has to be kept high to the degree sufficient to avoid distortion of the projected image of the target from its original shape.

In the disclosure of Japanese Unexamined Patent Application Publication No. 2017-196036, it has been discovered that the excessive noise interferes with measurement of the marker position even if the gradation processing is executed. Therefore, the intensity of the fluoroscopic radiation has to be kept high to the degree sufficient to measure the marker position by executing the gradation processing.

In the above-described circumstances, it is an object of the present invention to provide a moving object tracking apparatus, a radiotherapy system, and a moving object tracking method for accurate detection of the object to be tracked, and decrease in the load to the fluoroscopic radiation detector even under the severe fluoroscopic radiation conditions in the presence of excessive noise.

The present invention provides a radiotherapy system that includes an irradiation apparatus that generates and irradiates a radiation, two or more paired fluoroscopic apparatuses each including a fluoroscopic radiation detector and a fluoroscopic radiation generator in a pair for picking up a fluoroscopic image of an object to be tracked, a central control section for controlling the irradiation apparatus, and a moving object tracking control section for tracking a position of a moving object by detecting a position of the object to be tracked from the fluoroscopic image picked up by the fluoroscopic apparatuses. The moving object tracking control section executes an emphasizing process to emphasize an image with specific size in each of the fluoroscopic images derived from the two or more paired fluoroscopic apparatuses, obtains a value indicating a certainty degree of detection of a candidate position of the object to be tracked on the image subjected to the emphasizing process, extracts the candidate position based on the value indicating the certainty degree of detection, calculates a value indicating a correlation between the candidate position extracted from images picked up from two or more directions, and a position of the fluoroscopic radiation generator, detects the position of the object to be tracked based on the value indicating the certainty degree of detection, and the value indicating the correlation, and controls irradiation of the radiation to a target based on the detected position of the object to be tracked.

According to the present invention, in the case of severe fluoroscopic radiation conditions in the presence of excessive noise, the object to be tracked may be accurately detected, and the load to the fluoroscopic radiation detector may be decreased. The problem, the structure, and the effect other than those described above will be clarified by explanations to be described below.

DETAILED DESCRIPTION

A moving object tracking apparatus, a radiotherapy system, and a moving object tracking method according to an embodiment of the present invention will be described referring to FIG. 1 to FIG. 10.

Figure 1:
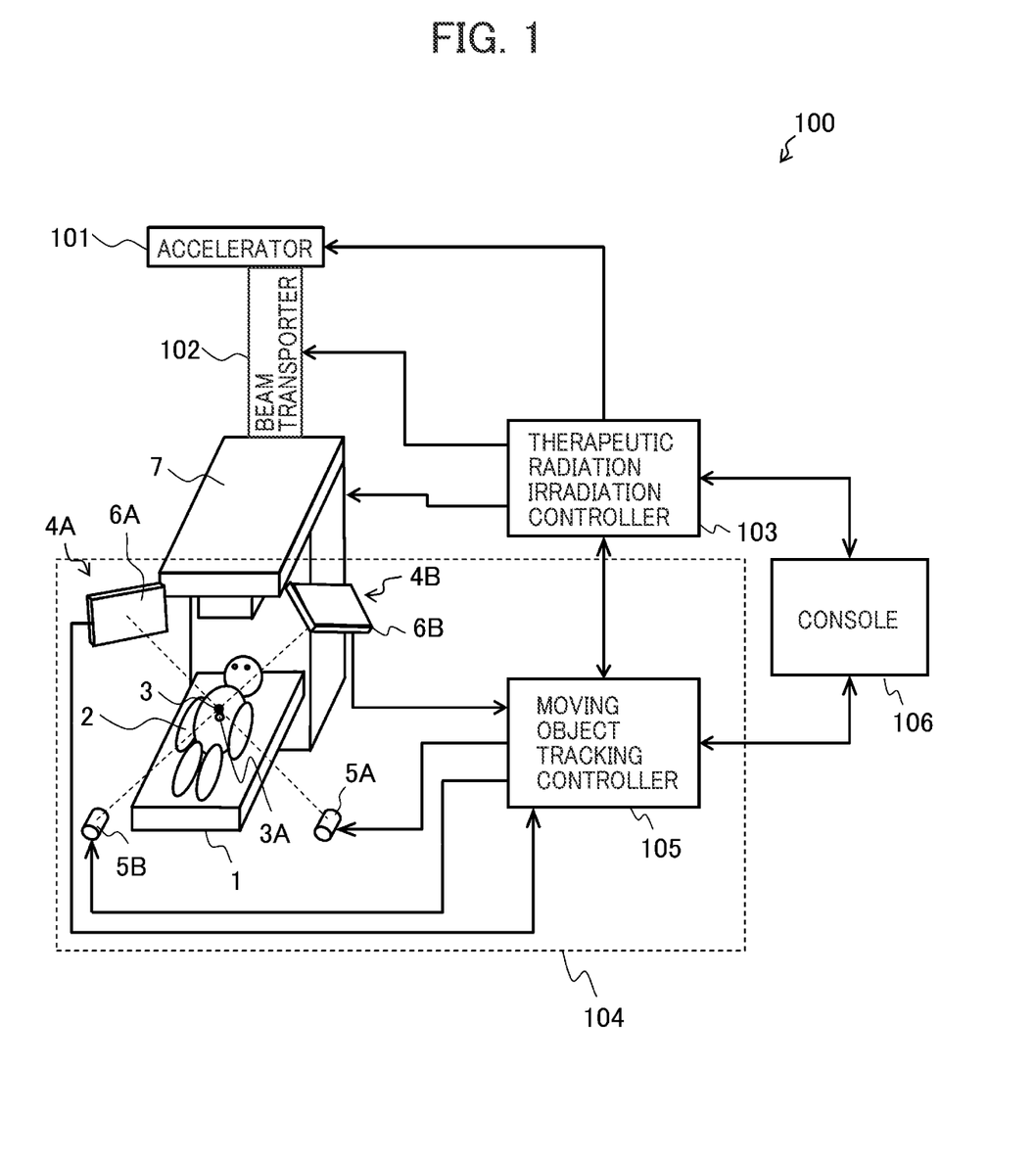
FIG. 1 illustrates an entire structure of a radiotherapy system according to an embodiment of the present invention.

An entire structure of a radiotherapy system 100 will be described referring to FIG. 1. FIG. 1 schematically shows an entire structure of the radiotherapy system of the embodiment.

Referring to FIG. 1, the radiotherapy system 100 is configured to irradiate a particle beam that contains baryon such as carbon ion, and proton to an affected part (hereinafter referred to as an irradiation target 3A) in a subject 2.

The radiotherapy system 100 includes an accelerator 101, a beam transporter 102, a bed 1 that allows positioning of the subject 2, a therapeutic radiation irradiation apparatus 7 for irradiating the therapeutic particle beam supplied from the accelerator 101 to the irradiation target 3A in the subject 2, a therapeutic radiation irradiation controller 103, a moving object tracking apparatus 104, a console 106, and the like.

A target 3 as the object to be tracked in the subject 2 is described as a marker implanted near the irradiation target 3A in the subject 2.

The therapeutic particle beam is accelerated by the accelerator 101 disposed in the room other than the treatment room to the required energy, and led by the beam transporter 102 to the therapeutic radiation irradiation apparatus 7. The accelerator 101 may be a synchrotron type accelerator, a cyclotron type accelerator, and various types of accelerators.

The therapeutic radiation irradiation apparatus 7 includes two paired scanning electromagnets, a dose monitor, and a position monitor (all are not shown). The two paired scanning electromagnets are disposed in the direction where each pair is orthogonal to each other so that the particle beam is bent to reach the desired position in the plane perpendicular to the beam axis at the target position. The dose monitor measures dose of the irradiated particle beam. The position monitor is capable of detecting the position through which the particle beam passes. The particle beam that has passed through the therapeutic radiation irradiation apparatus 7 reaches the irradiation target 3A.

The particle beam irradiation method is not limited to the particular method. It is possible to use the raster scanning method and the line scanning method for irradiating the fine particle beam without stopping the irradiation besides the spot scanning method in which the dose distributions is formed by arraying dose distribution constituted by fine particle beams adapted to the shape of the irradiation target 3A.

Besides the scanning methods as described above, the present invention may be applied to the irradiation method for forming the dose distribution adapted to the target shape using the collimator and the bolus after expanding the distribution of the particle beam by, for example, the wobbler method and the double scattered body method.

When using X-ray as the therapeutic radiation instead of the particle beam such as the carbon ion beam and the proton beam, a therapeutic X-ray irradiation apparatus for generating therapeutic X-ray is provided instead of the accelerator 101 and the beam transporter 102. When using γ-ray, a therapeutic γ-ray irradiation apparatus for generating therapeutic γ-ray is provided instead of the accelerator 101 and the beam transporter 102. When using the electron beam, a therapeutic electron beam irradiation apparatus for generating therapeutic electron beam is provided instead of the accelerator 101 and the beam transporter 102.

The moving object tracking apparatus 104 includes fluoroscopic radiographic devices 4A, 4B, and a moving object tracking controller 105.

The fluoroscopic radiographic device 4A includes a fluoroscopic radiation generator 5A for generating the fluoroscopic radiation to the target 3 in the subject 2 from a first direction, a fluoroscopic radiation detector 6A for detecting a two-dimensional dose distribution of the fluoroscopic radiation that has been generated from the fluoroscopic radiation generator 5A to permeate through the subject 2, and a signal processing circuit (not shown).

The fluoroscopic radiation detector 6A outputs an analog signal from two-dimensionally arrayed detecting elements. The signal processing circuit processes the analog signal from the fluoroscopic radiation detector 6A to generate data of the fluoroscopic images so that the generated data are transmitted to the moving object tracking controller 105.

Likewise, the fluoroscopic radiographic device 4B includes a fluoroscopic radiation generator 5B for generating the fluoroscopic radiation to the target 3 in the subject 2 from a second direction different from the first direction, a fluoroscopic radiation detector 6B for detecting the two-dimensional dose distribution of the fluoroscopic radiation that has been generated from the fluoroscopic radiation generator 5B to permeate through the subject 2, and a signal processing circuit (not shown).

The fluoroscopic radiation detector 6B outputs an analog signal from two-dimensionally arrayed detecting elements. The signal processing circuit processes the analog signal from the fluoroscopic radiation detector 6B to generate data of the fluoroscopic images so that the generated data are transmitted to the moving object tracking controller 105.

In the embodiment, the two fluoroscopic radiation detectors are used. However, the number of the fluoroscopic radiation detectors are not limited so long as the number is two or more.

The moving object tracking controller 105 executes an arithmetic operation to obtain a position of the target 3 based on signals of the fluoroscopic images input from the fluoroscopic radiographic devices 4A, 4B. Based on the position of the target 3, it is determined whether or not extraction of the therapeutic particle beam is permitted. The signal indicating the determination result on permission of irradiating the therapeutic particle beam is transmitted to the therapeutic radiation irradiation controller 103.

Figure 2:
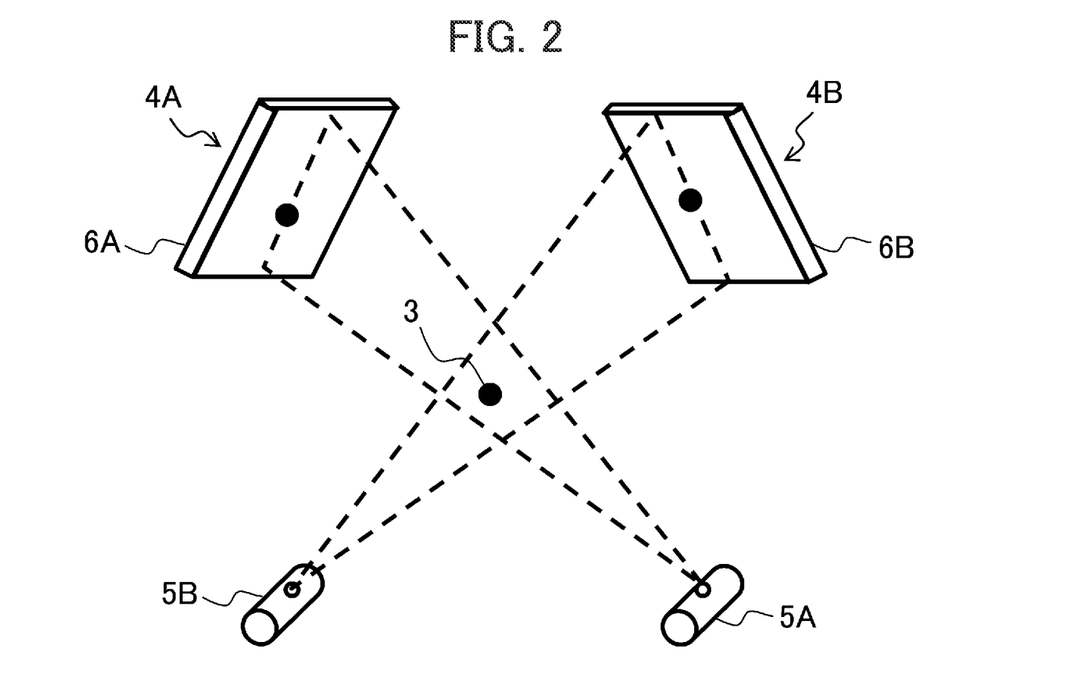
FIG. 2 is a conceptual view representing that a moving object tracking apparatus according to the embodiment acquires fluoroscopic images.

More specifically, the moving object tracking controller 105 irradiates radiation generated from the fluoroscopic radiation generator 5A to the target 3 as shown in FIG. 2. The fluoroscopic radiation detector 6A measures the two-dimensional dose distribution of the radiation that has passed through the target 3 so that the image of the target 3 is picked up. Simultaneously, the radiation generated from the fluoroscopic radiation generator 5B is irradiated to the target 3. The fluoroscopic radiation detector 6B measures the two-dimensional dose distribution of the radiation that has passed through the target 3 so that the image of the target 3 is picked up.

The moving object tracking controller 105 obtains a three-dimensional position of the target 3 from two fluoroscopic images that have been acquired. Based on the result, it is determined whether or not extraction of the therapeutic particle beam is permitted.

For example, the moving object tracking controller 105 determines whether or not the target 3 is positioned within a preliminarily designated gate range. If it is determined that the target 3 is positioned within the gate range, a gate-on signal is transmitted to the therapeutic radiation irradiation controller 103 to permit extraction of the particle beam to the irradiation target 3A. If it is determined that the target 3 is not positioned within the gate range, a gate-off signal is transmitted so as not to permit the extraction.

The moving object tracking controller 105 of the embodiment executes the process for detecting the target 3. The explanation of the process will be made later in detail.

The fluoroscopic images may be acquired by the fluoroscopic radiographic devices 4A, 4B at a constant interval of 30 Hz, for example. The target 3 is observed in the acquired fluoroscopic image. The process to be described later is executed to identify the position of the target 3 in the fluoroscopic image.

Because of the time required for searching the fluoroscopic images over the entire area, the position of the target 3 may be searched only in the range in a certain degree of spread from the center, that is, the position of the target 3 in the previous fluoroscopic image.

Figure 3:
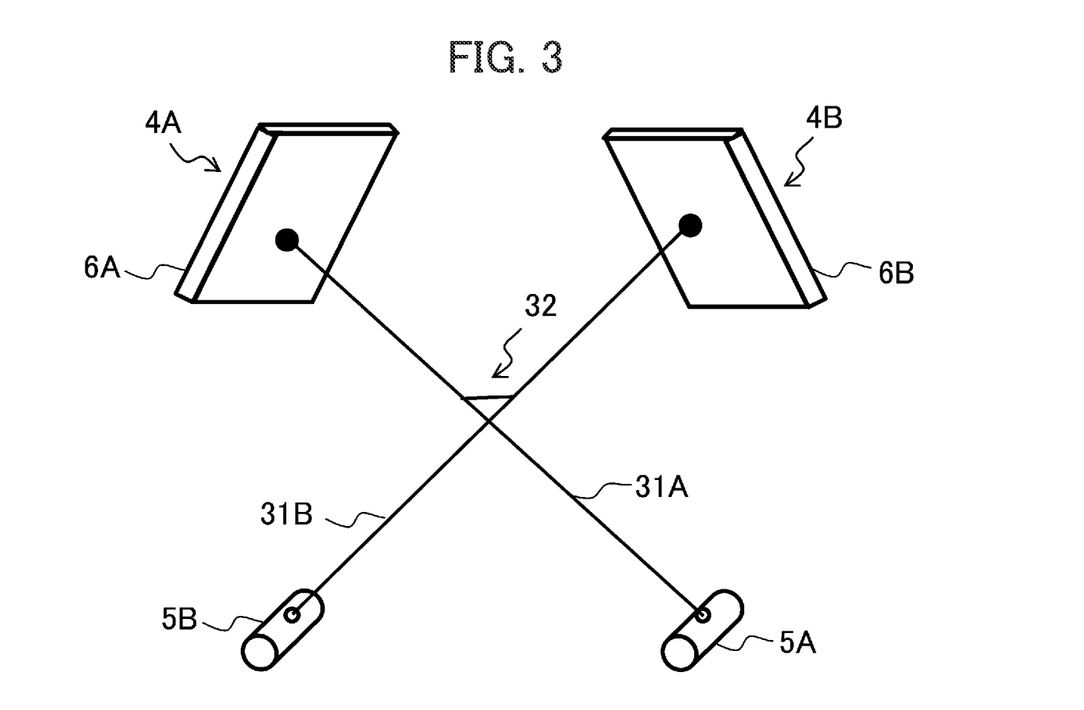
FIG. 3 is a schematic view representing that the moving object tracking apparatus according to the embodiment calculates a target position from the fluoroscopic images.

FIG. 3 shows a line 31A formed by connecting a position corresponding to the detected target 3 on the fluoroscopic radiation detector 6A and the fluoroscopic radiation generator 5A, and a line 31B formed by connecting a position corresponding to the target 3 on the fluoroscopic radiation detector 6B and the fluoroscopic radiation generator 5B. Ideally, those two lines intersect at one point. The intersection point represents the position of the target 3.

Actually, however, owing to detection error and the error in installation of the fluoroscopic radiation detector, those two lines are normally in a twisted relation rather than being intersected. The common perpendicular line may be drawn between positions at which those two lines in the twisted relation become proximate to each other. A midpoint of the common perpendicular line 32 is set as the three-dimensional position of the target 3.

Referring back to FIG. 1, the therapeutic radiation irradiation controller 103 is connected to the accelerator 101, the beam transporter 102, and the therapeutic radiation irradiation apparatus 7, and controls operations of the respective devices constituting the components.

The therapeutic radiation irradiation controller 103 or the moving object tracking controller 105 may be configured to allow the computer and FPGA (Field-Programmable Gate Array) with a CPU, a memory, an interface and the like to read programs, and to execute the calculation. The programs are stored in internal recording media in the respective components, or an external recording medium (not shown). The programs are read and executed by the CPU.

Operations of the therapeutic radiation irradiation controller 103 or the moving object tracking controller 105 may be controlled by executing the single program. The operations may be controlled by executing a plurality of individual programs, or arbitrarily combined programs. The program may be partially or entirely executed by the dedicated hardware, or modularized. The respective programs may be installed in the respective devices from the program distribution server, the internal storage medium, and the external storage medium.

The therapeutic radiation irradiation controller 103 or the moving object tracking controller 105 does not have to be formed as the independent component, but may be constituted by integrating and commonizing two or more components each configured to execute the allocated part of the processing. At least a part of the configuration may be wiredly connected, or connected via a wireless network.

The most essential feature of the embodiment is the processing method of detecting the target 3 using the moving object tracking controller 105. The method will be described referring to FIG. 4 and subsequent drawings.

In the generally employed method, one or more candidate positions of the target 3 are detected from the fluoroscopic images acquired by the fluoroscopic radiographic devices 4A, 4B so as to obtain the value indicating the certainty degree of candidate detection. The value indicating a correlation between the detected candidate positions of the target 3 from the fluoroscopic radiation detectors 6A, 6B is obtained. Based on the value indicating the certainty degree of detection and the value indicating the correlation, the three-dimensional position of the target 3 is detected.

The value indicating the certainty degree of detection may be set as a matching score derived from the template matching. In the template matching, a prepared template image of the target 3 is compared with the fluoroscopic image to calculate the degree of similarity to the template image, which is called the matching score. The degree of similarity such as a standardized cross correlation may be used as the matching score.

The higher the matching score becomes, the higher the matching between the fluoroscopic image in searching and the template image becomes. The position with the matching score higher than the prescribed threshold value is extracted as the candidate position of the target.

The value indicating the correlation is set as the length of the common perpendicular line (the common perpendicular line 32 as shown in FIG. 3). The common perpendicular line serves to link two lines by the shortest distance, that is, the line formed by connecting a position corresponding to the candidate position of the target 3 of the fluoroscopic image acquired by the fluoroscopic radiographic device 4A on the fluoroscopic radiation detector 6A, and the fluoroscopic radiation generator 5A, and the line formed by connecting a position corresponding to the candidate position of the target 3 of the fluoroscopic image acquired by the fluoroscopic radiographic device 4B on the fluoroscopic radiation detector 6B, and the fluoroscopic radiation generator 5B.

In the above-described method, if positions of the target 3 projected on the fluoroscopic radiation detectors 6A, 6B are not extracted as the candidate positions of the target 3, the image with similar structure (the image incidentally generated by noise) to that of the target 3 may be recognized by mistake. The inventors of the present invention have clarified the need of keeping the intensity of the fluoroscopic radiation high to some extent for the reason as described above.

Figure 4:
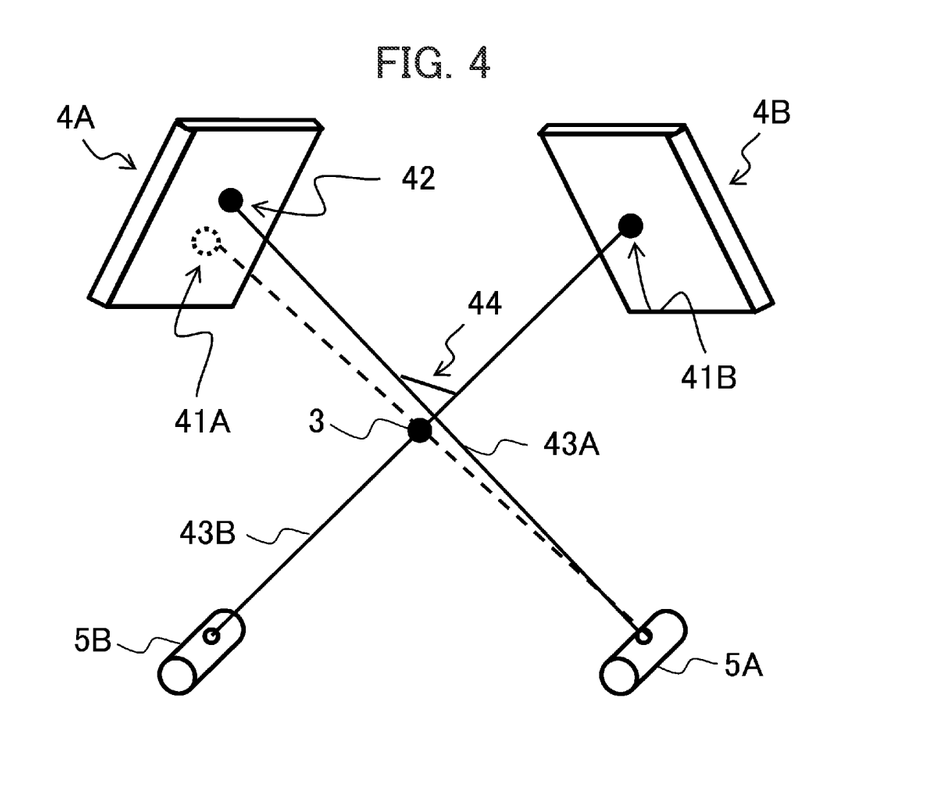
FIG. 4 is a schematic view representing the misdetection of noise in the fluoroscopic image.

Referring to FIG. 4, an explanation will be made about the reason for the need of keeping the intensity of the fluoroscopic radiation high to some extent in the generally employed method.

Referring to FIG. 4, because of low intensity of the fluoroscopic radiation, a projected image 41A of the target 3 on the fluoroscopic radiographic device 4A is buried in noises, and an image 42 with similar structure to that of the target 3 exists near the projected image 41A of the target 3. Meanwhile, a projected image 41B of the target 3 is clearly formed on the fluoroscopic radiographic device 4B.

In the case as shown in FIG. 4, the projected image 41A of the target 3 on the fluoroscopic radiographic device 4A is not detected as the candidate position of the target 3 from the template matching. The image 42 with the similar structure to that of the target 3 is only detected as the candidate position of the target 3.

In this case, the length of a common perpendicular line 44 for linking a line 43A formed by connecting the image 42 and the fluoroscopic radiation generator 5A, and a line 43B formed by connecting the image 41B and the fluoroscopic radiographic generator 5B takes a large value. However, as there is no other candidate position of the target 3, the image 42 is recognized as the projected image of the target 3 by mistake.

It has been found that the intensity of the fluoroscopic radiation is required to be kept high to some extent sufficient to prevent the projected image 41A of the target 3 from being buried in noises for avoiding the misrecognition.

In the embodiment, the target emphasizing process is applied to emphasize the image with specific size among the fluoroscopic images derived from the two or more paired fluoroscopic radiographic devices 4A, 4B for the purpose of further reducing the intensity of the fluoroscopic radiation, and further decreasing the operation load to the fluoroscopic radiation generator. In the above-described condition, the candidate positions of the target are calculated to detect the target position using the value indicating the certainty degree of detection, and the length of the common perpendicular line.

The process for extracting the specific frequency component from the fluoroscopic image is executed in accordance with the size of the target 3 as an example of the target emphasizing process according to the embodiment.

Specifically, one or more filters may be selected from a bandpass filter, a low pass filter, and a high pass filter. The parameter of the selected filter is specified in accordance with the size of the target 3.

For example, if the target 3 is a spherical marker with diameter of 2 mm, the projected image of the target 3 is formed as an image with its size of approximately 10 pixels in the fluoroscopic image. In this case, the parameter of the bandpass filter is set to emphasize the image with the size ranging from 5 to 15 pixels.

The target emphasizing process in the embodiment includes the process of averaging the specific region in accordance with the size of the target 3 in addition to the process of extracting the specific frequency component from the fluoroscopic image.

Specifically, one or more filters may be selected from an averaging filter, a median filter, and a Gaussian filter. The parameter of the selected filter is specified in accordance with the size of the target 3.

For example, if the target 3 is the spherical marker with diameter of 2 mm, the projected image of the target 3 is formed as an image with its size of approximately 10 pixels in the fluoroscopic image. In this case, the filter size of the averaging filter is set to approximately 3×3 pixels to emphasize the projected image of the target.

The target emphasizing process allows various types of filters to be combined to provide further advantageous effects.

Specifically, if the target 3 is the spherical marker with diameter of 2 mm, the projected image of the target is formed as an image with its size of approximately 10 pixels in the fluoroscopic image. In this case, a first averaging image and a second averaging image are generated. The first averaging image is formed by applying the averaging filter with its size set to 15×15 pixels. The second averaging image is formed by applying the averaging filter with its size set to 3×3 pixels. Then the difference between the first and the second averaging images is obtained to execute the process for emphasizing the specific frequency component.

Figure 5A:
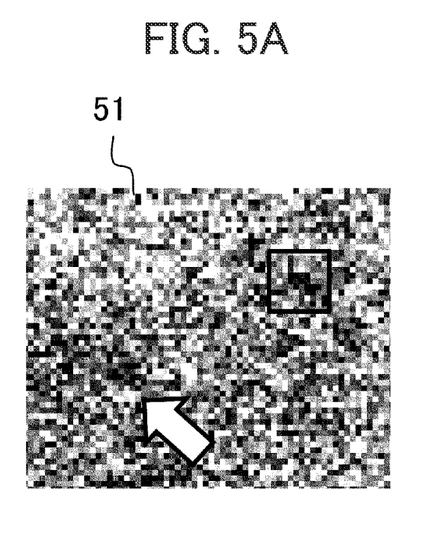
FIG. 5A is a view showing an example of the fluoroscopic image before application of an emphasizing process by the moving image tracking apparatus of the embodiment.
Figure 5B:
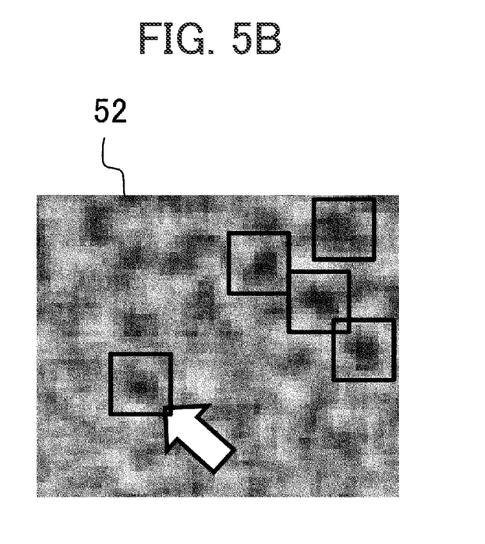
FIG. 5B is a view showing an example of the fluoroscopic image after application of the emphasizing process by the moving image tracking apparatus of the embodiment.

FIG. 5A shows an example of a fluoroscopic image 51 before applying the target emphasizing process. FIG. 5B shows an example of a fluoroscopic image 52 after applying the target emphasizing process. In this example, the target 3 is a spherical gold marker with diameter of 2 mm, and the bandpass filter is employed for executing the target emphasizing process. Referring to FIG. 5A and FIG. 5B, each projected image of the target 3 is indicated by a white arrow mark, and candidate positions of the target 3 extracted by the template matching are enclosed by black frames.

As FIG. 5A shows, the fluoroscopic image 51 before applying the target emphasizing process has the projected image of the originally circular shaped target 3 largely distorted. Therefore, the image is not extracted as the candidate position of the target 3.

As FIG. 5B shows, the fluoroscopic image 52 after applying the target emphasizing process has the projected image of the target 3 similar to the original circular image. As a result, the matching score becomes high, and such image is extracted as the candidate position. Application of the target emphasizing process may lower possibility of failing to extract the projected image of the target 3 as the candidate position.

Simultaneously, as FIG. 5B shows, in the fluoroscopic image 52 after applying the target emphasizing process, the images each with similar structure to that of the target 3 are extracted as the candidate positions. In the case of the images with similar structures, the length of the common perpendicular line relative to the candidate position of the target 3 derived from the other fluoroscopic radiation detector takes a large value. The use of the common perpendicular line distinguishes the projected image of the target 3 from other images.

The above-described effect allows lowering of possibility of misdetecting the image with the similar structure to that of the target 3 even if the intensity of the fluoroscopic radiation is reduced.

Figure 6A:
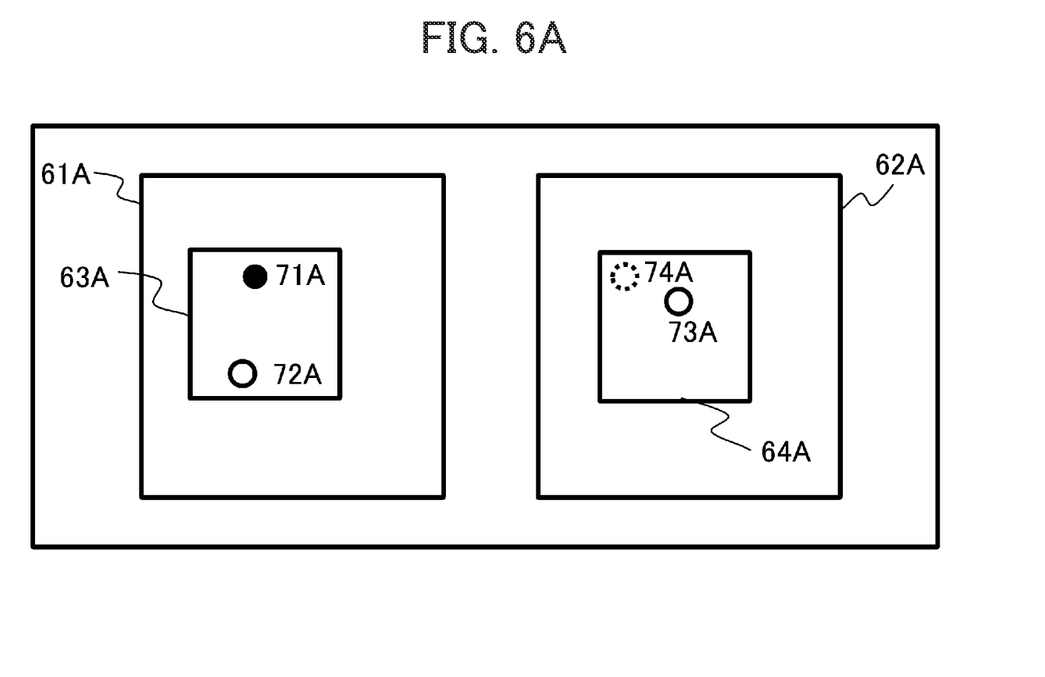
FIG. 6A is a view showing an example that the fluoroscopic images before application of the emphasizing process are displayed on a console according to the embodiment.
Figure 6B:
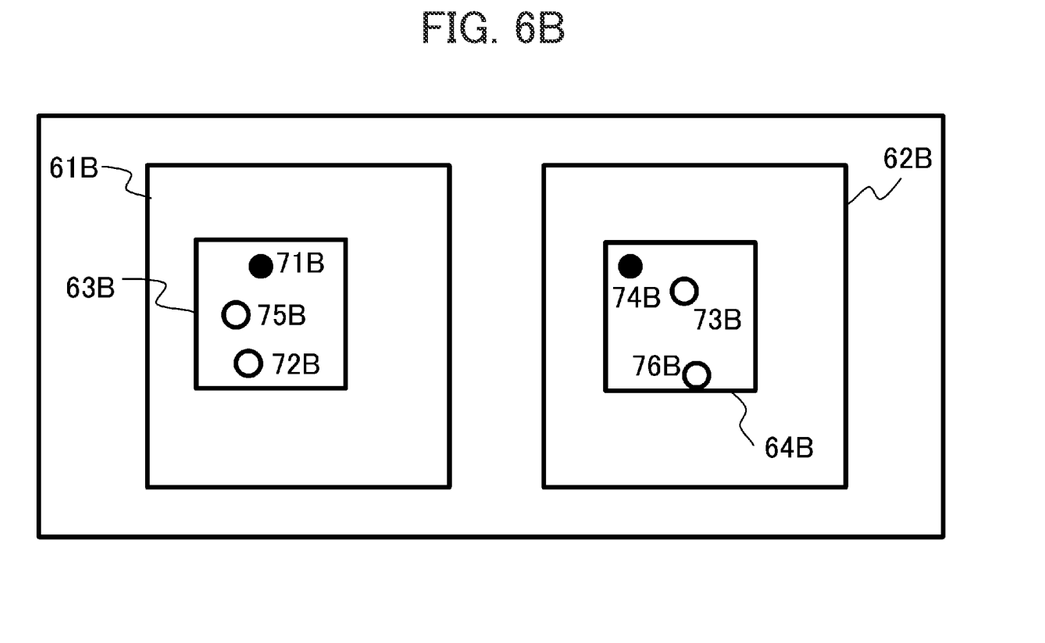
FIG. 6B is a view showing an example that the fluoroscopic images after application of the emphasizing process are displayed on the console according to the embodiment.

Referring to FIG. 6A and FIG. 6B, operations of the embodiment will be described in detail. FIG. 6A shows a fluoroscopic image 61A derived from the fluoroscopic radiographic device 4A, and a fluoroscopic image 62A derived from the fluoroscopic radiographic device 4B. FIG. 6B shows fluoroscopic images 61B, 62B after applying the target emphasizing process.

There are search areas 63A, 64A, 63B, 64B in the respective fluoroscopic images.

Referring to the fluoroscopic image 61A as shown in FIG. 6A, points 71A and 72A are extracted as the candidate positions of the target 3 in the search area. It is assumed that the point 71A as a filled circle corresponds to the actual projected image of the target 3. The point 72A indicates the image that has been incidentally formed by noise to have the similar shape to that of the target 3.

Referring to the fluoroscopic image 62A as shown in FIG. 6A, a point 73A is extracted as the candidate position of the target 3 in the search area. Although the projected image of the target 3 is actually formed at the position indicated by a dotted lined circle 74A, the image is buried in noises on the fluoroscopic image 62A derived from the fluoroscopic radiographic device 4B before applying the emphasizing process. Therefore, the point 74A is not extracted as the candidate position of the target 3.

Referring to the fluoroscopic image 61B after applying the emphasizing process as shown in FIG. 6B, points 71B, 72B, 75B are extracted as the candidate positions of the target 3 in the search area. The point 71B as the filled circle is the actual projected image of the target 3. Referring to FIG. 6A, the point 75B has not been extracted as the candidate on the fluoroscopic image 61A. Meanwhile, as FIG. 6B shows, the point 75B is newly extracted on the fluoroscopic image 61B. Those points are emphasized images of noise with similar structure to that of the target 3.

Referring to the fluoroscopic image 62B as shown in FIG. 6B, points 73B, 74B, 76B are extracted as candidate positions of the target 3 in the search area. The point 74B as the filled circle is the actual projected image of the target 3. Referring to FIG. 6A, the point 76B has not been extracted as the candidate on the fluoroscopic image 62A. Meanwhile, as FIG. 6B shows, the point 76B is newly extracted on the fluoroscopic image 62B after applying the emphasizing process. Those points are emphasized images of noise with similar structure to that of the target 3.

The moving object tracking controller 105 lists the candidate positions of the target 3 extracted from the respective fluoroscopic images. If a group including candidates of the target determined as identical exists in the list prepared from the fluoroscopic images, the candidate with the highest matching score is recognized as the candidate of the target 3 in the group of the list. It is preferable to delete the remaining candidates in the group from the list.

Among the candidates each with approximating size to that of the target 3, the candidate with the highest score is selected, and the remaining candidates are deleted from the list. It is possible to preliminarily set the reference range on the console 106, based on which it is determined that the identical candidates have been selected for deleting the approximating candidates.

The moving object tracking controller 105 calculates the length of the common perpendicular line with respect to all combinations of the listed candidates.

The evaluation function F is obtained by the following formula:

$$F = w_A \times S_A W_B \times S_B + w_L \times (1/L);$$

where $S_A$ denotes the score to the fluoroscopic image derived from the fluoroscopic radiographic device 4A, $S_B$ denotes the score to the fluoroscopic image derived from the fluoroscopic radiographic device 4B, and L denotes the length of the common perpendicular line. Each of $w_A$, $w_B$, $w_L$ as a weighting to the corresponding term is set from the console 106.

The moving object tracking controller 105 selects the combination having the maximum evaluation function F from all the combinations. The midpoint of the common perpendicular line of the selected combination is detected as the position of the target 3.

The moving object tracking controller 105 controls the particle beam to be irradiated to the irradiation target 3A based on the detected position of the target 3. For example, the moving object tracking controller 105 outputs a therapeutic particle beam irradiation signal to the therapeutic radiation irradiation controller 103 for irradiating the particle beam when the object to be tracked is positioned within the preliminarily designated range. The therapeutic radiation irradiation controller 103 then controls extraction of the particle beam.

Figure 7A:
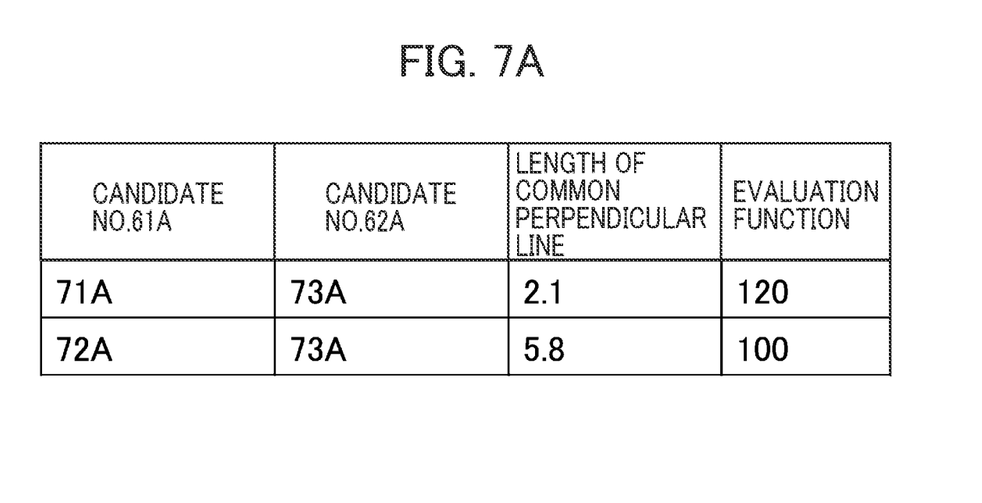
FIG. 7A represents an example of arithmetic results of an evaluation function before application of the emphasizing process according to the embodiment.
Figure 7B:
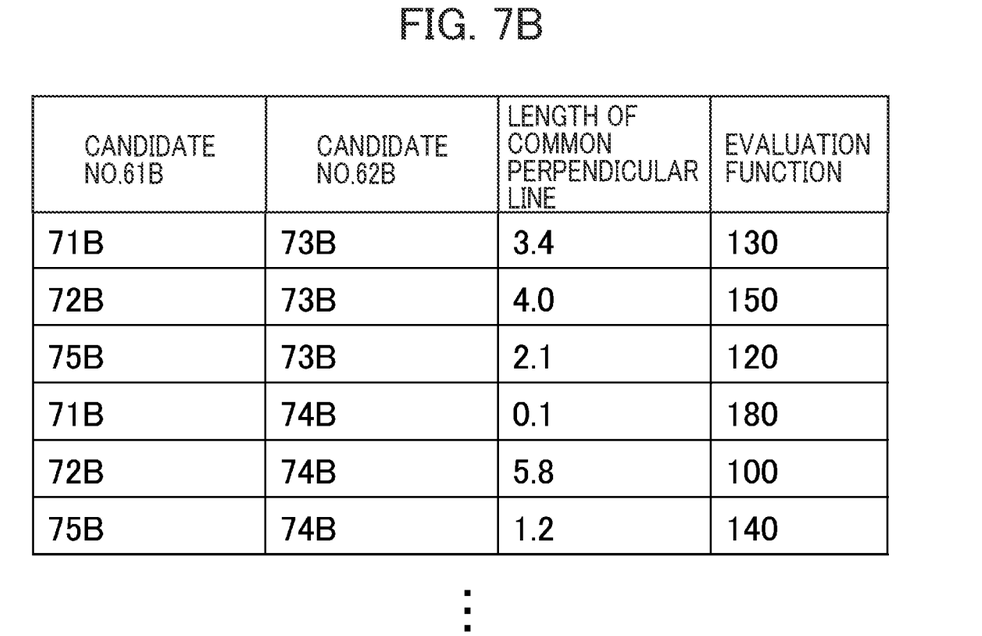
FIG. 7B represents an example of the arithmetic results of the evaluation function after application of the emphasizing process according to the embodiment.

FIG. 7A shows a list of candidate combinations of the target, which has been prepared from the fluoroscopic images 61A, 62A before applying the emphasizing process. FIG. 7B shows a list of candidate combinations of the target, which has been prepared from the fluoroscopic images 61B, 62B after applying the emphasizing process.

Referring to the list of FIG. 7A, the projected image of the target 3 is not extracted as the candidate from the fluoroscopic image 62A. Although the combination with the highest evaluation function F is selected, the point 73A as the noise is detected by mistake.

Referring to the list of FIG. 7B as a result of the emphasizing process according to the embodiment, the combination with the highest evaluation function F, that is, the combination of the point 71B of the fluoroscopic image 61B and the point 74B of the fluoroscopic image 62B is selected as the target 3. This may prevent the misdetection.

Referring back to FIG. 1, the console 106 is connected to the therapeutic radiation irradiation controller 103 and the moving object tracking controller 105, and displays the information on the screen based on the signal acquired from the controllers as described above. The console 106 receives an input from an operator who operates the radiotherapy system, and transmits various control signals to the therapeutic radiation irradiation controller 103 and the moving object tracking controller 105.

For example, the console 106 displays the fluoroscopic images derived from the fluoroscopic radiographic devices 4A, 4B, and a tracking condition of the target 3. The parameter required for tracking the target 3 may be set from the console 106.

Figure 8A:
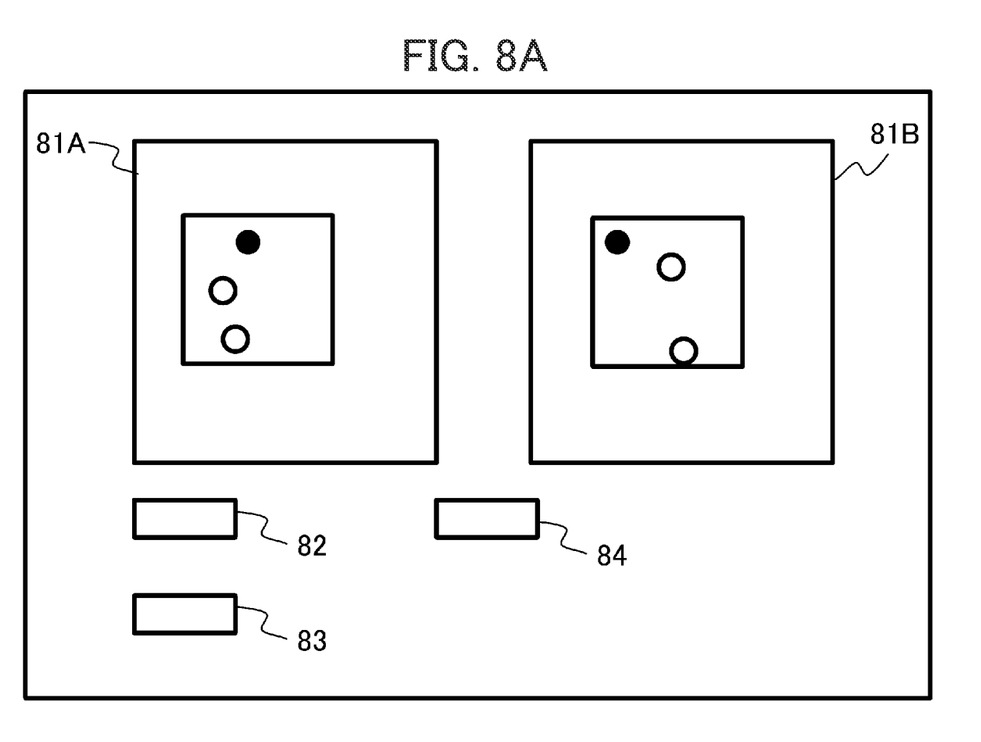
FIG. 8A is a conceptual view showing an example of a display of the console according to the embodiment.

FIG. 8A shows a screen to be displayed on the console 106 for tracking the moving object in association with the moving object tracking controller 105. Referring to FIG. 8A, a fluoroscopic image 81A derived from the fluoroscopic radiographic device 4A, and a fluoroscopic image 81B derived from the fluoroscopic radiographic device 4B are displayed on the screen of the console 106. A fluoroscopy start button 82, a set button 83, and an emphasizing button 84 are displayed at the lower section on the screen. Pressing the emphasizing button 84 as shown in FIG. 8A allows selection between ON and OFF for executing the emphasizing process.

Figure 8B:
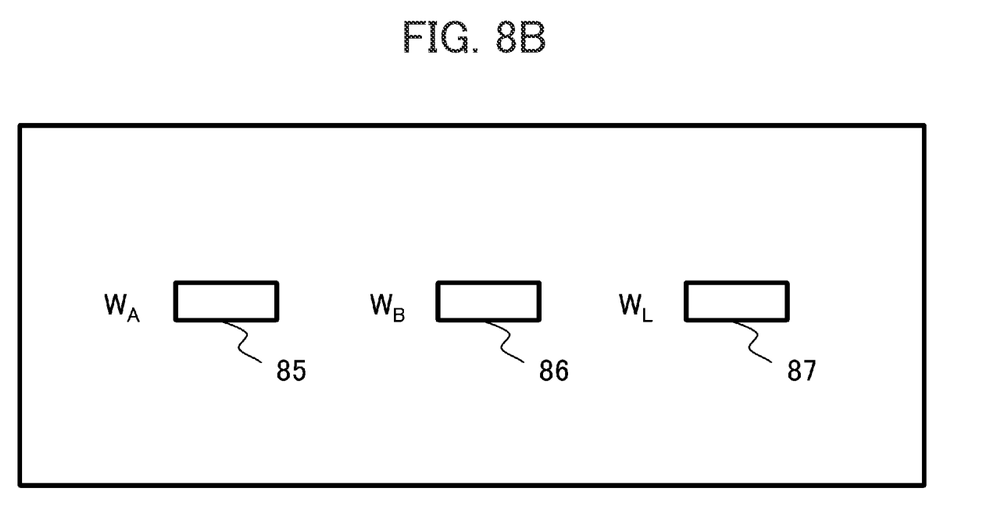
FIG. 8B is a conceptual view showing another example of the display of the console according to the embodiment.

The screen as shown in FIG. 8B is displayed by pressing the set button 83 of FIG. 8A. The screen as shown in FIG. 8B displays a $w_A$ input section 85, a $w_B$ input section 86, and $w_L$ input section 87, respectively for weighting the evaluation function as described above.

Figure 9:
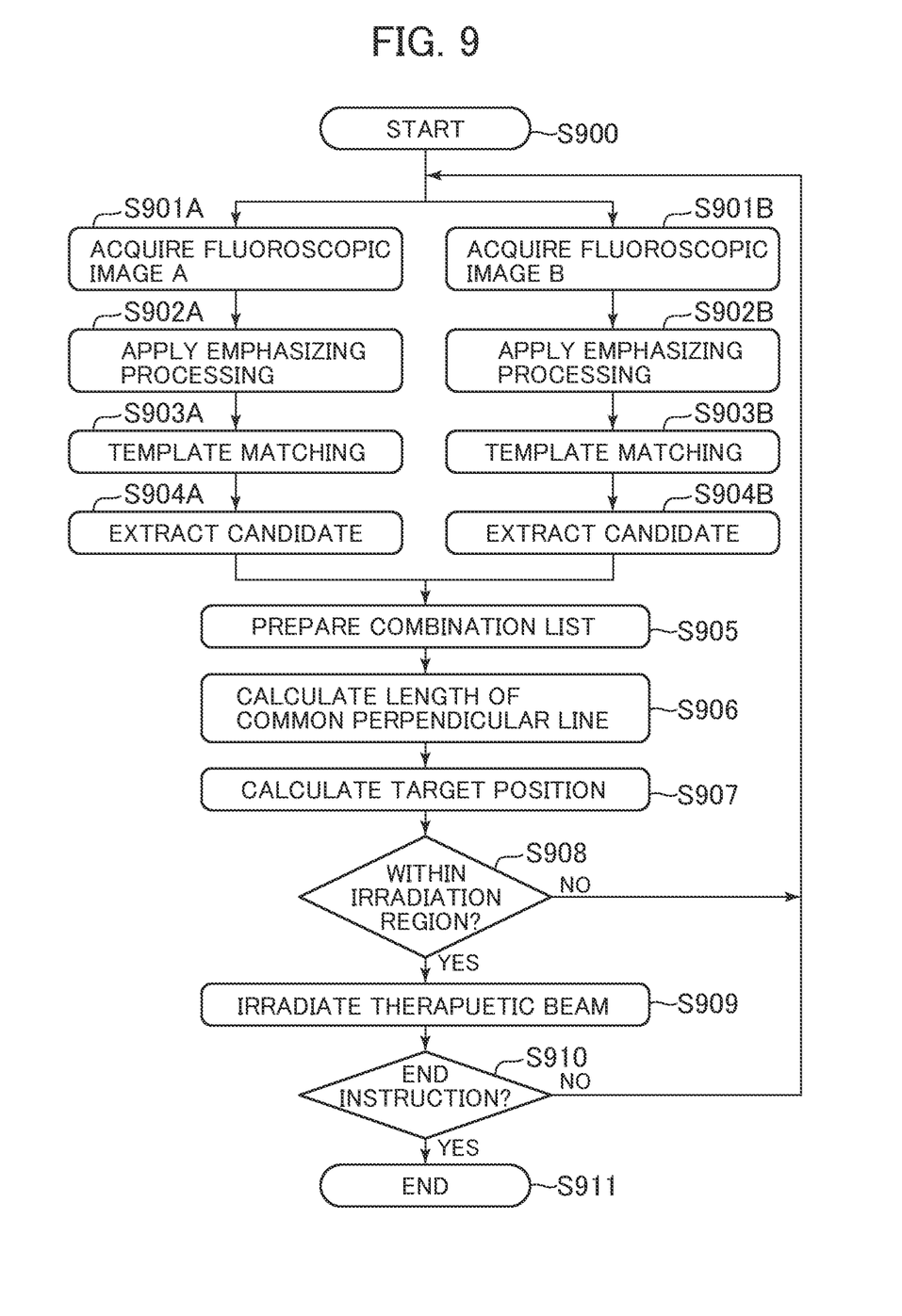
FIG. 9 is a flowchart of process steps of a real-time tumor tracking radiotherapy.

The operation flow for irradiating the therapeutic particle beam using the radiotherapy system according to the embodiment will be described referring to FIG. 9.

The bed 1 on which the subject 2 is restrained is moved so that the subject 2 is carried to a preliminarily planned position. At this time, the fluoroscopic images are picked up by the fluoroscopic radiation detectors 6A, 6B to confirm that the subject 2 has moved to the preliminarily planned position.

The moving object tracking controller 105 recognizes that the operator has pressed the fluoroscopy start button 82 on the console 106 (step S900). Subsequent to the confirmation, irradiation of the fluoroscopic radiation is started to allow the fluoroscopic radiographic device 4A to acquire a fluoroscopic image A, and the fluoroscopic radiographic device 4B to acquire a fluoroscopic image B (step S901A, S901B).

The moving object tracking controller 105 applies the emphasizing process to the acquired fluoroscopic images A and B (steps S902A, S902B). The matching scores to the emphasizing processed fluoroscopic images A, B are calculated by the template matching (steps S903A, S903B).

The moving object tracking controller 105 extracts the candidate positions of the target 3 from the fluoroscopic images A and B based on the calculated matching scores (steps S904A, S904B).

Thereafter, the moving object tracking controller 105 prepares a combination list based on the extracted candidate positions (step S905) so as to calculate each length of the common perpendicular lines with respect to all the combinations (step S906). Based on the calculated length values of the common perpendicular lines and the matching scores, the moving object tracking controller 105 calculates the three-dimensional position of the target 3 by executing the process as described above (step S907).

The moving object tracking controller 105 determines whether or not the target 3 is positioned in a gate range (irradiation region) (step S908). If Yes is obtained (the target 3 is positioned in the gate range) in step S908, the moving object tracking controller 105 outputs the therapeutic particle beam irradiation signal to the therapeutic radiation irradiation controller 103, and executes the particle beam extraction control to the therapeutic radiation irradiation apparatus 7 so that the therapeutic particle beam is irradiated to the irradiation target 3A (step S909).

Meanwhile, if No is obtained (the target 3 is not positioned in the gate range) in step S908, the moving object tracking controller 105 returns to steps S901A, S901B.

The therapeutic radiation irradiation controller 103 determines whether or not a processing end instruction exists (whether there is a specific instruction of the operator, or an instruction to terminate the moving object tracking at the end of therapeutic particle beam irradiation upon termination of the designated irradiation by the therapeutic radiation irradiation apparatus 7) (step S910).

If Yes is obtained (end instruction exists) in step S910, the therapeutic radiation irradiation controller 103 stops the fluoroscopic radiographing and the therapeutic particle beam irradiation to terminate the real-time tumor tracking radiotherapy.

Meanwhile, if No is obtained (end instruction does not exist) in step S910, the therapeutic radiation irradiation controller 103 returns to steps S901A, S901B to continue the real-time tumor tracking radiotherapy.

The advantageous effects of the embodiment will be described.

The radiotherapy system 100 according to the embodiment includes the accelerator 101 for generating and irradiating radiation, the beam transporter 102, the therapeutic radiation irradiation apparatus 7, two or more paired fluoroscopic radiographic devices 4A, 4B having pairs of the fluoroscopic radiation detectors 6A, 6B and the fluoroscopic radiation generators 5A, 5B, respectively for picking up fluoroscopic images of the target 3, the therapeutic radiation irradiation controller 103 for controlling the accelerator 101, the beam transporter 102, the therapeutic radiation irradiation apparatus 7, and the moving object tracking controller 105 for tracking the moving object position by detecting the position of the target 3 from the fluoroscopic images picked up by the fluoroscopic radiographic devices 4A, 4B. The moving object tracking controller 105 emphasizes images each with specific size in the fluoroscopic images acquired by the two or more paired fluoroscopic radiographic devices 4A, 4B. Then the value indicating the certainty degree in detecting the candidate positions of the target 3 is obtained in reference to the emphasized images. Based on the certainty degree of detection, the candidates are extracted so as to calculate the value indicating the correlation between the candidate positions extracted from the images picked up from two or more directions, and positions of the fluoroscopic radiation generators 5A, 5B, respectively. Based on the value indicating the certainty degree of detection, and the value indicating the correlation, the position of the target 3 is detected. The radiation to be irradiated to the irradiation target 3A is controlled based on the detected position of the target 3.

Even under the severe conditions for fluoroscopic radiographing owing to thickness of the subject 2, the moving object tracking apparatus 104 is capable of continuously tracking the target 3 without being missed even in the presence of excessive noise. This makes it possible to reduce the intensity of the fluoroscopic radiation compared with the generally employed system by lowering the possibility of missing the target 3, and to decrease the operation loads to the fluoroscopic radiation generators 5A, 5B compared with the generally employed system.

Reduction in the intensity of the fluoroscopic radiation may decrease the exposed dosage of the subject 2.

As possibility of missing the target 3 may be lowered, the operator does not have to operate the moving object tracking apparatus 104 to redetect the target 3 with high accuracy in the case of missing the target 3. Therefore, the irradiation time may be reduced.

As the moving object tracking controller 105 determines the size of the image to be emphasized in accordance with the size of the target 3 in the emphasizing process, the target 3 may be emphasized with higher accuracy, thus further lowering the possibility of missing the target 3.

The moving object tracking controller 105 extracts the specific frequency component in accordance with the size of the target 3 from the fluoroscopic image to emphasize the image with specific size by using the filter for extracting the specific frequency component from the image, that is, one or more filters selected from the bandpass filter, the low pass filter, and the high pass filter. This may further lower the possibility of missing the target 3.

The moving object tracking controller 105 averages the specific region of the fluoroscopic image in accordance with the size of the target 3 to emphasize the image with specific size by using the filter for averaging the specific region, that is, one or more filters selected from the averaging filter, the median filter, and the Gaussian filter. This may further lower the possibility of missing the target 3.

The value indicating the correlation is set as the shortest length of the common perpendicular line 32 that connects two or more lines each extending between the candidate position of the target 3 on the fluoroscopic image, and the position of the fluoroscopic radiation generator 5A or 5B. As described above, the target 3 may be misdetected owing to increase in the length of the common perpendicular line. The use of the length of the common perpendicular line that indicates the correlation makes it possible to improve accuracy of detecting the target 3, resulting in reduced frequency of misdetection.

The moving object tracking controller 105, and the therapeutic radiation irradiation controller 103 irradiate the therapeutic particle beam when the target 3 is positioned in the preliminarily designated range. This makes it possible to improve accuracy of irradiating the particle beam to the irradiation target 3A.

The value indicating the certainty degree of detection is set as the matching score derived from the template matching. It is therefore possible to execute the high speed recognizing process, and to search the target 3 while being distinguished from the image similar to the target 3 with respect to the emphasizing processed fluoroscopic images. The possibility of missing the target 3, thus may further be lowered.

The moving object tracking controller 105 weights the value indicating the certainty degree of detection, and the value indicating the correlation. Based on the weighting result, the position of the target 3 is detected. It is possible to accurately detect the position of the target 3 even under the severe X-ray image pickup condition, further contributing reduction in the irradiating time.

OTHER EXAMPLE

The present invention is not limited to the above-described embodiment, but may be variously modified and applied. The embodiment has been described for readily understanding of the present invention, and is not limited to the structure provided with all components as described above.

The embodiment has been described that the matching score and the common perpendicular line are weighted, based on which the position of the target 3 is detected. If a plurality of candidate positions each with higher matching score than the predetermined value are obtained from the respective fluoroscopic images, the plurality of common perpendicular lines are obtained. The moving object tracking controller 105 may be configured to detect the candidate position with the matching score corresponding to the shortest common perpendicular line from those obtained as the position of the target 3.

The structure as described above reduces the frequency of missing the target 3. It is therefore possible to decrease the operation loads to the fluoroscopic radiation generators 5A, 5B.

The embodiment has been described that the method for extracting the candidate position is implemented based on the matching score derived from the template matching.

In the method of extracting the candidate position of the target 3 as another example, the moving object tracking controller 105 may be configured to set a first region including two or more first pixels around an interest pixel for each of the fluoroscopic images, and a second region including one or more second pixels that are different from the two or more first pixels, and calculate the likelihood that becomes large as values of two or more first pixels approximate to one another, and values of two or more first pixels and the values of one or more second pixels are separated farther. Based on the likelihood, the candidate position is extracted.

The structure as described above reduces the frequency of missing the target 3. It is therefore possible to decrease the operation loads to the fluoroscopic radiation generators 5A, 5B.

The length of the common perpendicular line is used as the value indicating the correlation. However, the length of any other element maybe used instead of the common perpendicular line.

Figure 10:
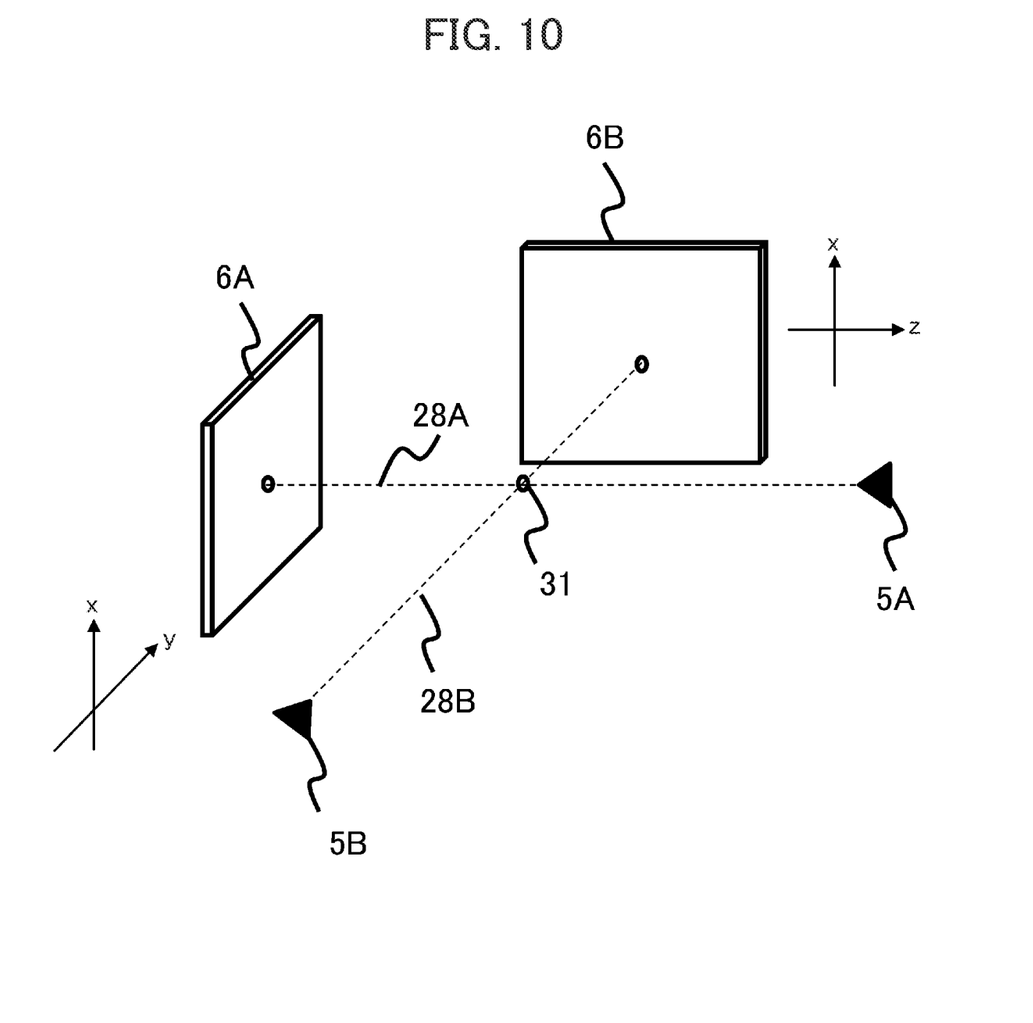
FIG. 10 is a conceptual view representing that a moving object tracking apparatus as another example of the embodiment calculates the marker position from the fluoroscopic images.

For example, referring to FIG. 10, it is assumed that the fluoroscopic images A and B are generated as the axes orthogonal to each other, and those images A and B are projected on the xy plane and the xz plane, respectively.

In FIG. 10, a dotted line 28A indicates a straight line extending from the fluoroscopic radiation generator 5A while passing through an isocenter 31, and a dotted line 28B indicates a straight line extending from the fluoroscopic radiation generator 5B while passing through the isocenter 31. In this case, the dotted line 28A that connects the positions of the fluoroscopic radiation detector 6A and the fluoroscopic radiation generator 5A is orthogonal to the dotted line 28B that connects the positions of the fluoroscopic radiation detector 6B and the fluoroscopic radiation generator 5B. As the x-axis is a common axis, ideally, the x-coordinates of the target 3 of the images A and B derived from the template matching coincide with each other. Actually, however, the coordinates may be brought into an uncoincident state.

The difference in the x-coordinate between the images A and B may be used instead of the length of the common perpendicular line. The x-axis in this case is referred to as the common axis, and the difference in the x-axis coordinates is referred to as the length of the common axis. The use of the length of the common axis as the value indicating the correlation allows reduction in the frequency of missing the target 3.

If the two fluoroscopic images are not perpendicular to each other, straight lines parallel to those images may be obtained. In this case, the difference between the straight lines as the common axes may be used instead of the length of the common perpendicular line.

In the embodiment as described above, the spherical target 3 is used. However, the target 3 may have a coiled shape.

In the embodiment, the use of the target 3 as the object to be tracked has been explained. The object to be tracked is not limited to the target 3. The irradiation target 3A may be directly detected without using the target 3. The object to be tracked may be the high density area in the subject 2, for example, the bone such as ribs.

Instead of the gate irradiation, the irradiation method may be the tracking type irradiation for tracking the irradiation position based on the position of the target 3 and the like. For example, in the case of tracking type X-ray irradiation, the direction of the X-ray generator for forming distribution is changed in accordance with movement of the target so that the X-ray irradiation position is changed in accordance with the movement of the target. In the case of the particle beam, the tracking irradiation may be performed by adjusting the amount of excitation of the scanning electromagnet in alignment with the target position.

There may be the case that it is difficult to detect the target 3 on anyone of the two fluoroscopic images. In such a case, on the other fluoroscopic image where the target 3 is easily detected, the candidate with the highest matching score is only tracked. The candidate positions of the target 3 are listed to include only those derived from the fluoroscopic image where it is difficult to detect the target 3 in the similar way to the generally employed process. Based on the respective matching scores and length values of the common perpendicular lines, the target 3 may be detected. The candidates of the target 3 derived from the other fluoroscopic image are narrowed down to one candidate so as to reduce the misdetection while reducing the calculation time.

What is claimed is:

1. A radiotherapy system comprising:
    an irradiation apparatus that generates and irradiates a radiation;
    two or more paired fluoroscopic apparatuses each including a fluoroscopic radiation detector and a fluoroscopic radiation generator in a pair for picking up a fluoroscopic image of an object to be tracked;
    a central control section for controlling the irradiation apparatus; and
    a moving object tracking control section for tracking a moving object by detecting a position of the object from the fluoroscopic image picked up by the fluoroscopic apparatuses, wherein the moving object tracking control section:
    executes an emphasizing process to emphasize an image with specific size in each of the fluoroscopic images derived from the two or more paired fluoroscopic apparatuses;
    obtains a value indicating a certainty degree of detection of a candidate position of the object to be tracked on the image subjected to the emphasizing process;
    extracts the candidate position based on the value indicating the certainty degree of detection;
    calculates a value indicating a correlation between the candidate position extracted from images picked up from two or more directions, and a position of the fluoroscopic radiation generator;
    detects the position of the object to be tracked based on the value indicating the certainty degree of detection, and the value indicating the correlation; and
    controls irradiation of the radiation to a target based on the detected position of the object to be tracked.

2. The radiotherapy system according to claim 1, wherein the moving object tracking control section determines a size of the image to be emphasized in accordance with a size of the object to be tracked in execution of the emphasizing process.

3. The radiotherapy system according to claim 1, wherein the moving object tracking control section executes the emphasizing process to emphasize the image with specific size by extracting a specific frequency component in accordance with the size of the object to be tracked.

4. The radiotherapy system according to claim 3, wherein the moving object tracking control section executes the emphasizing process to emphasize the image with specific size by using one or more filters selected from a bandpass filter, a low pass filter, and a high pass filter for extracting the specific frequency component from the image.

5. The radiotherapy system according to claim 1, wherein the moving object tracking control section executes the emphasizing process to emphasize the image with specific size by averaging a specific region of the fluoroscopic image in accordance with the size of the object to be tracked.

6. The radiotherapy system according to claim 5, wherein the moving object tracking control section executes the emphasizing process to emphasize the image with specific size by using one or more filters selected from an averaging filter, a median filter, and a Gaussian filter for averaging the specific region.

7. The radiotherapy system according to claim 1, wherein the value indicating the correlation is selected from one of a length of a common perpendicular line that links two or more lines by the shortest distance, each formed by connecting the candidate position on the fluoroscopic image and a position of the fluoroscopic radiation generator, and a length of the common perpendicular line that links two or more lines by the shortest distance, each formed by connecting the candidate position on the fluoroscopic image and the fluoroscopic radiation generator.

8. The radiotherapy system according to claim 1, wherein the value indicating the certainty degree of detection is a matching score derived from a template matching, or a likelihood calculated for each interest pixel contained in the fluoroscopic image.

9. The radiotherapy system according to claim 1, wherein the moving object tracking control section applies weightings to the value indicating the certainty degree of detection, and the value indicating the correlation, and detects the position of the object to be tracked based on weighting results.

10. The radiotherapy system according to claim 1, wherein the object to be tracked is one of a marker for identifying the target, the target itself, and a high-density region.

11. The radiotherapy system according to claim 1, wherein the moving object tracking control section and the central control section are configured to irradiate the radiation when the object to be tracked is positioned within a preliminarily designated range.

12. A moving object tracking apparatus comprising:
two or more paired fluoroscopic apparatuses each including a fluoroscopic radiation detector and a fluoroscopic radiation generator in a pair for picking up a fluoroscopic image of an object to be tracked; and
a moving object tracking control section for tracking a position of a moving object by detecting a position of the object to be tracked from the fluoroscopic image picked up by the fluoroscopic apparatuses, wherein the moving object tracking control section:
executes an emphasizing process to emphasize an image with specific size in each of the fluoroscopic images derived from the two or more paired fluoroscopic apparatuses;
obtains a value indicating a certainty degree of detection of a candidate position of the object to be tracked on the image subjected to the emphasizing process;
extracts the candidate position based on the value indicating the certainty degree of detection;
calculates a value indicating a correlation between the candidate position extracted from images picked up from two or more directions, and a position of the fluoroscopic radiation generator; and
detects the position of the object to be tracked based on the value indicating the certainty degree of detection, and the value indicating the correlation.

13. A moving object tracking method comprising:
picking up a fluoroscopic image of an object to be tracked by two or more paired fluoroscopic apparatuses each including a fluoroscopic radiation detector and a fluoroscopic radiation generator in a pair;
executing an emphasizing process to emphasize an image with specific size in each of the fluoroscopic images derived from the two or more paired fluoroscopic apparatuses;
obtaining a value indicating a certainty degree of detection of a candidate position of the object to be tracked on the image subjected to the emphasizing process;
extracting the candidate position based on the value indicating the certainty degree of detection;
calculating a value indicating a correlation between the candidate position extracted from images picked up from two or more directions, and a position of the fluoroscopic radiation generator; and
detecting the position of the object to be tracked based on the value indicating the certainty degree of detection, and the value indicating the correlation.

* * * * *